United States Patent [19]

Milligan et al.

[11] 4,341,898
[45] Jul. 27, 1982

[54] SYNTHESIS OF ISOCYANATES FROM NITROALKANES

[75] Inventors: Barton Milligan, Coplay; Robert K. Pinschmidt, Jr., Allentown, both of Pa.

[73] Assignee: Air Products and Chemicals, Inc., Allentown, Pa.

[21] Appl. No.: 264,253

[22] Filed: May 18, 1981

[51] Int. Cl.³ ............... C07C 118/00; C07C 125/063; C07C 125/07
[52] U.S. Cl. .................... 560/24; 260/453 P; 560/25
[58] Field of Search ............. 260/453 P; 560/24, 25

[56] References Cited

U.S. PATENT DOCUMENTS

| | | | |
|---|---|---|---|
| 3,461,149 | 8/1969 | Hardy et al. | 260/453 |
| 3,674,827 | 7/1972 | Rao et al. | 260/453 |
| 3,914,268 | 10/1975 | Yamahara et al. | 260/453 |
| 3,925,435 | 12/1975 | Crosby et al. | 260/453 |
| 3,931,106 | 1/1976 | Crosby et al. | 260/46.5 |
| 4,029,686 | 6/1977 | Crosby et al. | 260/453 |
| 4,145,360 | 3/1979 | Crosby et al. | 260/453 |

OTHER PUBLICATIONS

Georg Trickes et al., Catalyzed Rearrangement of Nitrile Oxides to Isoeyanates, *Angew. Chem. Int. Ed. Engl.* 16, 1977, No. 8, p. 555.
Abdur Rahman et al., *Pakistan Journal of Scientific Research*, Complete Volume, (30), 1978, pp. 92-94.
Ch. Grundmann, *The Nitrile Oxides—Versatile Tools of Theoretical and Preparative Chemistry*, 1979, pp. 52 and 53.

*Primary Examiner*—Dolph H. Torrence
*Attorney, Agent, or Firm*—Michael Leach; E. Eugene Innis; James C. Simmons

[57] ABSTRACT

A process for the preparation of aromatic isocyanates from nitroalkanes. A nitromethyl aromatic compound of the general formula:

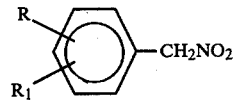

wherein R and $R_1$ represent hydrogen, halogen, a $C_1$-$C_5$ alkyl radical, a $C_1$-$C_4$ alkoxy radical, nitro, isocyanato, an alkoxycarbonylamino, or nitromethyl radical, with R and $R_1$ being the same or different, is heated in the presence of an effective amount of a Lewis acid or Bronsted acid substance to effect a dehydrogenation-isomerization reaction to yield an aromatic isocyanate of the general formula:

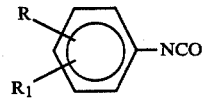

The product of the reaction may be recovered as the aromatic isocyanate or the alcohol adduct, a carbamate.

16 Claims, No Drawings

SYNTHESIS OF ISOCYANATES FROM NITROALKANES

TECHNICAL FIELD

The present invention relates to a process for preparing organic isocyanates from nitroalkanes. More particularly, the invention relates to a process for preparing aromatic isocyanates from phenyl nitromethanes.

BACKGROUND OF THE PRIOR ART

Enormous quantities of organic isocyanates are produced and consumed annually. Isocyanates find use in the preparation of urethane foam, coatings, pesticides and the like. The majority of isocyanates sold in the United States and world-wide comprises toluene diisocyanate (TDI)—usually in 80:20 mixture of the 2,4- and 2,6-isomers—and methylenediphenyl diisocyanate (MDI, predominantly the 4,4'-isomer) in a mixture with its higher oligomers, polymethylenepolyphenylene isocyanate (PMPPI).

Commercially, the most widely used method for preparing aromatic isocyanates is the phosgenation route which comprises the reduction of a nitroaromatic compound to the aromatic amine followed by reaction with phosgene to yield the aromatic isocyanate. The phosgene reaction is usually conducted at elevated temperatures and pressures. The phosgenation route is long, energy intensive and must handle highly corrosive materials such as hydrogen chloride, chlorine, sulfuric acid and nitric acid, and toxic reagents and intermediates such as nitroaromatic compounds, aromatic amines, chlorine and phosgene. The materials used in the construction of the process equipment also tend to the exotic in order to avoid chloride corrosion.

A new route which offers an alternative to the chlorine and hydrogen chloride which are generated in the phosgenation process is the carbonylation of the corresponding nitroaromatic compound as taught, for example, in U.S. Pat. Nos. 3,461,149; 3,674,827 and 3,914,268.

U.S. Pat. Nos. 3,925,435; 3,931,106; 4,029,686; and 4,145,360 disclose the production of isocyanates by the thermal decomposition of furoxanes.

The rearrangement of nitrile oxides to isocyanates using sulfur dioxide as a catalyst is taught by G. Trickes and H. Meier, Angew. Chem., Int. Ed. Eng., 16, 555 (1977).

A. Rahman et al., Pakistan Journal of Scientific Research, Vol. 30, 91 (1978), disclose that the reaction of nitroethane with acetic anhydride/triethylamine in nonpolar solvents like ether or benzene, yields dimethyl furoxane and that of phenyl nitromethane with acetic anhydride/triethylamine in ether or benzene yields diphenyl furoxane. The authors state that the formation of furoxane in these reactions is an evidence of the intermediacy of a nitrile oxide.

Nitrile oxides are prepared from primary nitroparaffins by a one-step reaction under mild conditions using phenylisocyanate as the dehydrating agent in the presence of catalytic amounts of triethylamine. See *The Nitrile Oxides*, Ch. Grundman and P. Grunanger, Springer-Verlag New York, 1971, p. 52.

The above references disadvantageously require at least a stoichiometric amount of dehydrating agent which is consumed in the process.

There is a need for an efficient non-chloride method for producing aromatic isocyanates from nitroalkanes since the carbonylation process is still long and energy intensive.

There is yet a need for a method for making aromatic isocyanates from nitro compounds in a basically one-step process.

Further, there is a need for the ability to generate aromatic isocyanates from nitromethyl aromatic compounds.

There is still a further need for a route that quickly and efficiently generates isocyanate precursors in advantageous oxidation states and utilizes inexpensive dehydration chemistry instead of multiple oxidation-reduction sequences to prepare isocyanates from nitroalkanes.

SUMMARY OF THE INVENTION

The above needs have been met by our invention of a process for the preparation of aromatic isocyanates from nitromethyl aromatic compounds. The process comprises:

(a) heating a compound of the general formula I

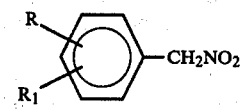

wherein R and $R_1$ represent hydrogen, halogen, nitro, a $C_1$-$C_5$ alkyl radical, a $C_1$-$C_4$ alkoxy radical, isocyanato, an alkoxycarbonylamino group of the formula —NH—COOR$_2$ wherein $R_2$ represents a $C_1$-$C_5$ alkyl radical, or a nitromethyl radical, with R and $R_1$ being the same or different, in the presence of an effective amount of a Lewis acid or Bronsted acid substance to yield an aromatic isocyanate of the general formula II

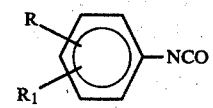

wherein R and $R_1$ are the same as in general formula I; provided that if R or $R_1$ were a nitromethyl radical in general formula I, such R or $R_1$ now represents an isocyanato group; and (b) recovering the aromatic isocyanate.

Advantageously, the aromatic isocyanate may be recovered in an alkyl alcohol-containing medium to afford an alkyl carbamate of the general formula III:

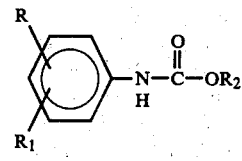

wherein R, $R_1$ and $R_2$ are the same as in general formula II provided that if R or $R_1$ represented an isocyanato group in general formula II, such R or $R_1$ now represents an alkoxycarbonylamino group of the formula —NH—COOR$_2$.

Preferably, in the above general formulas I, II and III, R and $R_1$ independently or simultaneously represent hydrogen, halogen, a $C_1$-$C_3$ alkyl radical, or a nitromethyl radical which nitromethyl radical is transformed into an isocyanato group in general formula II and an alkoxycarbonylamino group in general formula III. Especially preferred are aromatic compounds in which R and $R_1$ independently or simultaneously are a nitromethyl radical or hydrogen.

DETAILED DESCRIPTION OF THE INVENTION

The process of this invention is applicable to nitromethyl aromatic compounds of general formula I which comprise phenyl nitromethane or a substituted phenyl nitromethane wherein the phenyl group is mono- or di-substituted with, for example, a $C_1$–$C_5$ alkyl radical, halogen, nitro, a $C_1$–$C_4$ alkoxy radical, isocyanato, an alkoxycarbonylamino radical, or a nitromethyl radical. Halogen and nitromethyl are preferred substituents on the aromatic ring.

The halogen may be fluorine, chlorine, bromine or iodine; preferably chlorine or bromine.

The alkyl group may be, for example, methyl, ethyl, n-propyl, isopropyl, n-butyl, isobutyl, t-butyl, n-pentyl, isopentyl, or neopentyl. Methyl is the preferred alkyl substituent. Examples of suitable alkoxy groups are methoxy, n-propoxy, isopropoxy, n-butoxy, t-butoxy and n-pentoxy.

Illustrative examples of suitable nitromethyl aromatic compounds which can be used as a reactant in the process of this invention are the following:

1. Alpha-nitrotoluene
2. 2-bromo-nitromethylbenzene
3. 3-butoxy-nitromethylbenzene
4. 4-butyl-nitromethylbenzene
5. 3-chloro-nitromethylbenzene
6. 3,5-diethyl-nitromethylbenzene
7. 2,4-dinitro-nitromethylbenzene
8. 2,5-dinitro-nitromethylbenzene
9. 2,6-dinitro-nitromethylbenzene
10. 3,4-dinitro-nitromethylbenzene
11. 3,5-dinitro-nitromethylbenzene
12. 2-ethoxy-nitromethylbenzene
13. 2-ethyl-nitromethylbenzene
14. 4-fluoro-nitromethylbenzene
15. 4-isopropyl-nitromethylbenzene
16. 4-methoxy-nitromethylbenzene
17. 3-nitro-nitromethylbenzene
18. 4-propoxy-nitromethylbenzene
19. 3-propyl-nitromethylbenzene
20. 1,3-di(nitromethyl)benzene
21. 4-bromo-1,3-di(nitromethyl)benzene
22. 5-ethyl-1,3-di(nitromethyl)benzene
23. 4-methyl-1,3-di(nitromethyl)benzene
24. 5-nitro-1,3-di(nitromethyl)benzene
25. 1,4-di(nitromethyl)benzene
26. 2-bromo-1,4-di(nitromethyl)benzene
27. 2-ethyl-1,4-di(nitromethyl)benzene
28. 2-methyl-1,4-di(nitromethyl)benzene
29. 2-nitro-1,4-di(nitromethyl)benzene Alpha-nitrotoluene and the di(nitromethyl)benzenes are the preferred nitromethyl aromatic compounds for the reaction, with alpha-nitrotoluene most preferred.

The nitromethyl aromatic compounds may be prepared according to any route known in the art for introducing a nitro group into the methyl radical of a methyl aromatic compound, such as toluene or a xylene. Examples of known nitration reactions include using nitric acid in the presence of a reducing agent as taught in Japanese Patent Application No. SHO 45-51595; using nitrogen dioxide as taught in U.S. Pat. No. 2,401,525, U.S. Pat. No. 2,867,669 and U.S. Pat. No. 3,459,816; or reacting a monohalomethyl aromatic compound with a nitrite salt as taught in U.S. Pat. No. 3,544,640; which disclosures are incorporated by reference.

As would be obvious to a worker in the art, to obtain the substituted nitromethyl aromatic compounds of general formula I the correspondingly substituted toluenes and substituted xylenes are nitrated as described above. Again as a worker in the art would readily recognize, the substituent may have to be introduced into the aromatic ring after the nitration reaction in those cases where the conditions of the nitration reaction would also cause the substituent to undergo a reaction.

The inventive process comprises heating a nitromethyl aromatic compound of general formula I in the presence of an effective amount of a Lewis acid or Bronsted acid substance. An effective amount is that quantity which causes the nitromethyl aromatic compound to undergo a reaction at the temperature and pressure used to yield an aromatic isocyanate. The Lewis acid or Bronsted acid substance may be viewed, for the sake of convenience, as a "catalyst;" that is to say, a substance which affects the rate of a chemical reaction while remaining unchanged in chemical identity after the reaction is complete although some fraction of the "catalyst" may be consumed or changed in the process of this invention. The substance may function in some cases by being consumed and regenerated, while in other cases the substance may not enter the reaction and functions by virtue of some type of surface phenomenon. In addition, our use of the term "catalyst" is not to be restricted in such manner as to imply a "small" amount although a catalyst used in the process for preparing aromatic isocyanates may be present in a small amount as well as in stoichiometric amounts or greater, especially when the catalyst comprises the packing, or bed, of a gas phase reaction vessel.

A Lewis acid is a substance that can take up an electron pair to form a covalent bond—an electron pair acceptor. Examples of Lewis acids are compounds having less than a full octet of electrons, such as trimethyl boron, boron trifluoride and sulfur trioxide; positive ions, particularly polyvalent ions which are strongly hydrated in aqueous solution; compounds having double bonds excepting carbon-carbon double bonds, such as carbon dioxide and sulfur dioxide; and halide compounds in which the central atom may exceed its octet, such as stannic chloride, titanium tetrabromide, and molecular iodine.

A Bronsted acid is a substance which is a proton donor such as, for example the mineral acids hydrochloric acid, nitric acid, sulfuric acid and the like, as well as organic acids such as p-toluenesulfonic acid, trichloroacetic acid and the like.

A representative listing of Lewis acid and Bronsted acid substances, or "catalysts," useful in the process of the invention would include, by way of example, mineral acids such as hydrochloric acid, sulfuric acid, nitric acid; aliphatic and aromatic sulfonic acids such as methanesulfonic acid, benzene sulfonic acid and p-toluenesulfonic acid; aliphatic phosphonic acids such as methanephosphonic acid; acidic molecular sieves, aluminum silicates, acidic aluminas, silicas, zeolites, and metal salts and oxides including calcium sulfate. Other representative examples of Lewis acids and Bronsted acids are set forth in *Hard and Soft Acids and Bases Principle in Organic Chemistry*, Tse-Lok Ho, Academic Press, New York, 1977, which is incorporated by reference.

While we do not wish to be bound by a theory on the mechanism of the process, we believe it is a dehydration-isomerization reaction. We postulate the first step of the reaction to be the complexation of the Lewis acid, or the protonation in the case of a Bronsted acid, with an oxygen of the nitro group. Through a series of bond migrations hydrogen atoms attached to the carbon atom of the nitromethyl group are lost or transferred to the complexed oxygen atom. A molecule of water is then split out leaving behind an aromatic nitrile oxide compound which spontaneously or catalytically thermally isomerizes to the aromatic isocyanate.

The quantity of Lewis acid or Bronsted acid catalyst used in the reaction is somewhat empirical and can vary widely depending upon the type of catalyst used, as hereinafter discussed with respect to the class of dehydration-isomerization reaction, the reactivity of the catalyst and the reactivity of the reactants present.

The temperatures necessary for the dehydration-isomerization of the nitromethyl aromatic compounds of general formula I may vary from as low as about 50° C. to as high as about 500° C. depending upon the category of the dehydration-isomerization reaction as more fully described hereinafter. The reaction may take place in the gas or liquid phase. Accordingly, the pressures encountered during the process may range from subatmospheric to as high as 1000 psig. Needless to say, pressurized apparatus is utilized when superatmosphere pressures are encountered.

With respect to liquid phase reactions a solvent system is recommended although not necessary. The solvent or mixture of solvents which are used may be, for example, hydroxylic, aromatic, halogenated aromatic or oxygenated aliphatic compounds, mineral oils or silicone oils. With respect to gas phase reactions the nitromethyl aromatic compound may be injected neat or with a diluent into the reactor. For example, phenylnitromethane may be fed as a solution in toluene or methanol.

Advantageously, an inert gas is used to blanket the reaction medium to exclude oxygen. The inert gas may also serve as a carrier gas to convey the nitro compound through the catalyst packing material in a gas phase reactor, or to remove the isocyanate product from the reaction medium in a liquid phase reaction so that the product may be isolated or captured as the carbamate in an alcohol containing medium. Helium, argon or preferably nitrogen may serve as the inert blanketing atmosphere or carrier gas.

In general, the dehydration-isomerization process for making aromatic isocyanates may be further categorized according to reaction conditions and catalysts, i.e., Lewis acid or Bronsted acid substances. The three categories of dehydration-isomerization reactions are "gas phase", "liquid phase", and "liquid phase-solid catalyst".

The "gas phase" reaction involves dripping the nitromethyl aromatic compound usually in solution into a heated pyrolysis tube in a stream of carrier gas. The heated tube is packed with a catalyst. The product is desirably recovered by trapping in a cooled vessel containing an alcohol. The temperature of the heated reaction tube may range from 150° to about 500° C., preferably the lower range of 175° to 275° C., and the pressure may range from subatmospheric to atmospheric, such as 5 to 760 torr. The nitromethyl aromatic compound is injected into the reaction apparatus neat or, preferably, as a solution in toluene or methanol while utilizing nitrogen or helium as the carrier gas. Although any standard Lewis acid catalyst, including microglass beads, can form the packing in the heated reaction tube, molecular sieves are the preferred packing, specifically 3A and 5A molecular sieves.

The "liquid phase" reaction is conveniently performed in a reaction vessel such as a 3-necked round bottom flask or a stainless steel pressure reactor as necessary. The reaction vessel is heated to a temperature of from 50° to 250° C. while maintaining a pressure from subatmospheric to as high as 1000 psi with a pressure of 0.01 torr to 10 atm preferred. Mineral oil, silicone oil, aromatic and halogenated aromatic hydrocarbons and oxygenated aliphatic compounds are useful reaction solvents. Toluene and chlorobenzene are especially desirable. Catalysts include virtually any Lewis acid or Bronsted acid material, preferably mineral acids, aliphatic or aromatic sulfonic and phosphonic acids which may be present in amounts ranging from 1.0 to 95% or more.

The "liquid phase" reaction may be further subcategorized into "liquid phase-flash pyrolysis", "liquid phase-two phase" and "liquid phase-single phase" as described hereinafter.

The "liquid phase-solid catalyst" reaction is carried out at reflux in a reaction vessel, such as a 3-necked round bottom flask or a pressure reactor, at various temperatures which may range from 50° to 200° C., preferably 70° to 150° C., and pressures ranging from subatmospheric to 1000 psig, preferably 1 atm to 250 psig. Into the reaction vessel along with an aromatic hydrocarbon or a hydroxylic solvent is placed the required Lewis acid catalyst such as a molecular sieve, aluminum silicate, acidic alumina, silicas or metal salts and oxides such as calcium sulfate in amounts ranging, for example, from 1 to 200% of the nitromethyl compound. Nitrogen is provided as a blanketing and carrier gas.

Sulfur dioxide is optionally bubbled into the dehydration-isomerization reaction to catalyze the isomerization of the postulated aromatic nitrile oxide intermediate to the aromatic isocyanate.

Specific examples of aromatic isocyanates that may be prepared according to the inventive process include the following:
1. Phenylisocyanate
2. 2-bromo-phenylisocyanate
3. 3-butoxy-phenylisocyanate
4. 4-butyl-phenylisocyanate
5. 3-chloro-phenylisocyanate
6. 3,5-diethyl-phenylisocyanate
7. 2,4-dinitro-phenylisocyanate
8. 2,5-dinitro-phenylisocyanate
9. 2,6-dinitro-phenylisocyanate
10. 3,4-dinitro-phenylisocyanate
11. 3,5-dinitro-phenylisocyanate
12. 2-ethoxy-phenylisocyanate
13. 2-ethyl-phenylisocyanate
14. 4-fluoro-phenylisocyanate
15. 4-isopropyl-phenylisocyanate
16. 4-methoxy-phenylisocyanate
17. 3-nitro-phenylisocyanate
18. 4-propoxy-phenylisocyanate
19. 3-propyl-phenylisocyanate
20. phenyl-1,3-diisocyanate
21. 4-bromo-phenyl-1,3-diisocyanate
22. 5-ethyl-phenyl-1,3-diisocyanate
23. 4-methyl-phenyl-1,3-diisocyanate 24. 5-nitro-phenyl-1,3-diisocyanate
25. phenyl-1,4-diisocyanate
26. 2-bromo-phenyl-1,4-diisocyanate
27. 2-ethyl-phenyl-1,4-diisocyanate
28. 2-methyl-phenyl-1,4-diisocyanate
29. 2-nitro-phenyl-1,4-diisocyanate Phenyl isocyanate and the phenylenediisocyanates are the preferred products.

The following examples are presented to describe the invention more fully without any intention of being limited thereby:

PRESSURE REACTIONS

Pressure reactions were conducted in 128 ml stainless steel reactor (Parr Instrument Company) rated at 3,000 psig.

The reactor was outfitted with two outlet ports and a thermocouple well, one outlet port extended into the bottom of the bomb to allow various gases to be bubbled through the liquid phase or for sample removal.

ALPHA-NITROTOLUENE

The reaction was performed in a 3000 ml 3-neck flask. Oxygen was bubbled through 1750 ml of toluene plus 20 g of copper sulfate for 5 to 10 minutes. Gaseous $NO_2$ (35.5 g) and $O_2$ gas were bubbled into the toluene over a 4 hour period. The mixture was maintained at 90° C. during the addition and for an additional 30 minutes afterwards. About 10 ml of the product mixture was washed with water and analyzed by gas liquid partition chromatography (glpc). Alpha-nitrotoluene was observed as the major product.

Half of the toluene was washed two times with 150 ml of water and 100 ml of the residue was vacuum distilled yielding five fractions. The first two fractions consisted largely of toluene and benzaldehyde. The small intermediate third fraction was discarded. The fourth fraction, b.p. 67°–80.5° C. (3 torr, yellow) was alpha-nitrotoluene. The fifth fraction, b.p. 84°–95° C. (4 torr, about 3 ml) crystallized partially on cooling. The liquid was more alpha-nitrotoluene and the crystals were impure benzoic acid (glpc, mp).

The fourth (main) fraction was redistilled giving three fractions. Each analyzed by glpc and nmr as containing more than 80% alpha-nitrotoluene (total volume of alpha-nitrotoluene: about 5 ml).

Table 1 shows the conversion to be almost 70% with the product mixture being 57% alpha-nitrotoluene.

TABLE 1

Synthesis of α-Nitrotoluene
$NO_2/O_2/CuSO_4$
Toluene, 80°/4 hr.

| | Component % | Conversion % |
|---|---|---|
| Benzaldehyde | 18.1 | 12.6 |
| Benzyl Alcohol/Nitrite | 12.7 | 8.8 |
| α-Nitrotoluene | 57.0 | 39.7 |
| Peak, RT 520 | 1.3 | 0.9 |
| Peak, RT 71 | 10.0 | 6.9 |

GAS PHASE REACTION (Examples 1–19)

The reaction was performed by dripping alpha-nitrotoluene usually in solution into a heated packed quartz pyrolysis tube (1.37 inches O.D.×12 inches long) in a stream of carrier or reagent gas (see Table II).

The alpha-nitrotoluene was added by a syringe pump. Rates of injection as well as the packing catalyst are recorded on Table II.

The product was recovered by trapping in either a test tube or a flask containing ⅛ inch glass helices and methanol, both cooled with a liquid nitrogen/isopropyl alcohol slurry. On several occasions a heat gun was used to melt solidified products which blocked the bottom of the reaction tube.

The reaction tube contained varying heights of catalysts. A few runs were made at reduced pressures by connecting the outlet from the trap through a second trap to a vacuum system. One microliter samples from the methanol trap were combined with one microliter of naphthalene standard and analyzed by glpc. Results are shown in Table II and reveal that aromatic isocyanates can be prepared from nitrocompounds in a one-step process. The best run gave 4.1% methyl carbanilate. Recoveries were frequently poor and substantial coking and decomposition of the agents on the bed were observed in a number of cases.

TABLE II

GAS PHASE REACTION

| EXAMPLE | 1 | 2 | 3 | 4 | 5 | 6 |
|---|---|---|---|---|---|---|
| Temp. Range | 280°–285° | 270°–280° | 240°–260° | 350°–355° | 400°–410° C. | 450°–455° C. |
| Carrier Gas | He | $N_2$ | $N_2$ | | | |
| Reagent | | | $SO_2$(17 ml/min) | $SO_2$(6.2 ml/min) | $SO_2$(6.2 ml/min) | $SO_2$(6.2 ml/min) |
| Tube Packing | 10cm Class IV Micro Glass Beads | Same as Example 1 | 7cm same as Example 1 | Same as Example 3 | Same as Example 3 | 8cm Quartz Fines |
| Vacuum | 17 torr | 24 torr | 760 torr | 50 torr | 760 torr | 760 torr |
| Syringe Pump | none | none | none | 0.1 ml/min | Same as Ex. 4 | Same as Ex. 4 |
| Pyrolysis Tube Appearance | Light brown with some black streaks | Dark Brown | Dark Brown | Charred (Black) | Charred (Black) | Charred (Black) |
| Amount of α-NT | 1.2 g | 1.2 g | 0.57 g | 1.31 g | 1.24 g | 1.22 g |
| Product Color | Yellow (Turbid) | Amber (Turbid) | Colorless (Turbid) | Yellow (Turbid) | Green (Turbid) | Amber (Turbid) |
| % of Products vs. Starting Sample | | | | | | |
| % Recovery | 9.8% | 40% | 7.8% | 1.4% | 15.4% | 13.7% |
| α-Nitrotoluene | 11.4% | 10.1% | 9.6% | 1.8% | 6.3% | 3.3% |
| Phenyl Isocyanate | 0.2% | Trace | | 0.1% | 0.2% | |
| Methyl Carbanilate | 1.1% | 4.0% | 0.5% | 0.2% | 0.3% | 0.1% |
| Benzaldehyde | 1.1% | 4.0% | 1.2% | 0.3% | 3.9% | 3.3% |
| Benzyl Acetal | 2.4% | 6.3% | 0.6% | 0.1% | 2.7% | 3.0% |
| Methyl Benzoate | 1.5% | 2.7% | | 0.2% | 1.0% | |
| Benzonitrile | 2.0% | 7.7% | 1.2% | 0.3% | 2.8% | 2.4% |
| Benzyl Alcohol | | 0.3% | Trace | | 2.0% | Trace |

TABLE II-continued

GAS PHASE REACTION

|  |  |  |  |  |  |  |
|---|---|---|---|---|---|---|
| Bibenzyl | Trace |  | 0.5% | Trace | 1.1% | 0.7% |
| Aniline | 0.4% | Trace |  | 0.1% | 0.1% | 0.1% |
| Benzaldoxime |  |  |  |  |  |  |
| Stilbene |  |  |  |  |  |  |
| Benzamide | 0.7% | 3.7% | 0.5% | Trace | 0.1% | 1.3% |
| Oxadiazole | 0.5% | 4.7% | 0.7% | 0.1% | 0.4% | 1.0% |
| α-Nitrostilbene |  |  |  |  |  |  |
| Miscellaneous |  | 4.7% |  |  |  |  |

| EXAMPLE | 7 | 8 | 9 | 10 | 11 | 12 |
|---|---|---|---|---|---|---|
| Temp. Range | 445°–452° C. | 400°–415° | 275°–285° | 347°–355° | 225°–243° | 200°–235° |
| Carrier Gas | N$_2$ | N$_2$ | N$_2$ | N$_2$ | N$_2$ | N$_2$ |
| Gas Flow | 11cc/min | 12cc/min | 12cc/min | 12cc/min | 12cc/min | 12cc/min |
| Tube Packing | Same as Example 6 | 9cm quartz fines | 10cm 3A molec. sieve 28 mesh | Same as Example 9 | Same as Example 9 | Same as Example 9 |
| Vacuum |  |  |  |  |  |  |
| Syringe Pump | Same as Example 4 | .4ml/min | .4ml/min | Manual Injection | 4ml/min | 4ml/min |
| Pyrolysis Tube Appearance | Dark brown | Clean | Grey | Grey | Grey | Light Brown |
| Amount of α-NT | 1.35g | 1.0g in 10ml MeOH | 1.0g in 10ml MeOH | 1.0g in 10ml MeOH | 1.2g in 10ml MeOH | 1.0g in 10gm Toluene |
| Product Color | Yellow (Turbid) | Yellow | Yellow | Yellow | Yellow | Yellow |
| % of Products vs. Starting Sample |  |  |  |  |  |  |
| % Recovery | 8.7% | 19.8% | 30.0% | 60.0% | 31.5% | 59.1% |
| α-Nitrotoluene | 2.3% | 3.6% | 3.1% | 5.0% | 1.5% | 10.0% |
| Phenyl Isocyanate |  |  |  |  |  |  |
| Methyl Carbanilate | 0.6% | 0.6% | 1.5% | 2.0% | 0.5% | 3.8% |
| Benzaldehyde | 1.4% | 5.4% | 5.4% | 8.0% | 6.0% | 5.6% |
| Benzyl Acetal | 2.9% | 6.0% | 1.5% | 2.0% |  |  |
| Methyl Benzoate |  | 0.6% | 3.8% | 4.0% |  |  |
| Benzonitrile | 1.7% | 2.4% | 5.4% | 7.0% | 7.0% | 6.2% |
| Benzyl Alcohol | 0.6% | 1.2% |  | Trace |  |  |
| Bibenzyl | 0.4% | 2.4% | Trace |  |  | 1.9% |
| Aniline | Trace |  | Trace |  | Trace |  |
| Benzaldoxime |  |  |  | 2.0% |  |  |
| Stilbene |  |  | 5.4% | 16.0% | 7.0% | 8.8% |
| Benzamide | 0.2% | 1.2% | 0.7% | 3.0% | 2.5% | 6.9% |
| Oxadiazole | 0.4% |  |  | 1.0% |  | 1.9% |
| α-Nitrostilbene |  |  |  | 4.0% | 1.0% |  |
| Miscellaneous |  | 1.2% | 3.0% | 5.5% | 5.7% |  |

| EXAMPLE | 13 | 14 | 15 | 16 | 17 | 18 | 19 |
|---|---|---|---|---|---|---|---|
| Temp. Range | 339°–358° | 220°–236° | 178°–195° | 220°–227° | 195°–224° | 225°–251° | 135°–155° |
| Carrier Gas | N$_2$ | N$_2$ | N$_2$ | N$_2$ | N$_2$ | N$_2$ | N$_2$ |
| Gas Flow | 12cc/min | 12cc/min | 12cc/min | 12cc/min | 12cc/min | 12cc/min | 12cc/min |
| Tube Packing | Same as Ex 9 | 8cm 4A Molec Sieve, 28 Mesh | Same as Ex 14 | 8cm 5A Molec. Sieve, 28 Mesh | Same as Ex 16 | 9cm 13A Molec. Sieve, 28 Mesh | 9cm 13A MS, 28 Mesh |
| Vacuum |  |  |  | 55 TORR |  |  |  |
| Syringe Pump | 4ml/min | 4ml/min | 4ml/min | 4ml/min | 4ml/min | 4ml/min | .3 ml/min |
| Pyrolysis Tube Appearance | Grey | Grey | Grey | Black | Black | Brown | Brown |
| Amount of α-NT | 1.0 g/10g toluene | 1.0 g/5 g toluene | 1.0 g/4 g toluene | 1.0 g/4 g toluene | 1.0 g/4 g toluene | 1.0 g/4 g toluene | 1.0 g/5 g toluene |
| Product Color | Yellow | Yellow | Dark Yellow | Yellow | Dark Yellow | Yellow | Amber |
| % of Products vs. Starting Sample |  |  |  |  |  |  |  |
| % Recovery | 53.4% | 25.1% | 48.0% | 29.8% | 47.4% | 28.8% | 37.0% |
| α-Nitrotoluene | 6.9% | 6.3% | 11.4% | 15.2% | 14.0% | 11.4% | 16.2% |
| Phenyl Isocyanate |  |  |  |  |  |  |  |
| Methyl Carbanilate | 2.5% | 0.5% | 3.6% | 2.7% | 4.1% | 1.2% | 0.7% |
| Benzaldehyde | 6.3% | 2.8% | 4.8% | 2.2% | 5.8% | 3.6% | 3.8% |
| Benzyl Acetal |  |  | Trace |  |  |  |  |
| Methyl Benzoate |  |  |  |  |  |  |  |
| Benzonitrile | 6.3% | 4.0% | 6.0% | 2.2% | 6.4% | 4.2% | 5.4% |
| Benzyl Alcohol | Trace |  |  |  |  | Trace |  |
| Bibenzyl | Trace |  |  |  |  | Trace |  |
| Aniline | Trace | Trace | Trace | Trace | 0.5% |  |  |
| Benzaldoxime | 2.5% |  |  |  |  |  |  |
| Stilbene | 7.5% | 6.8% |  | 1.6% | 2.9% | 4.8% | 2.3% |
| Benzamide | 5.0% | 0.5% | 9.0% | 2.2% | 4.6% | 0.6% | 4.6% |
| Oxadiazole | 1.9% |  | 3.0% | 1.0% | 2.3% |  | 0.7% |
| α-Nitrostilbene | 6.9% |  | 3.0% | 2.2% | 4.1% | 1.2% | 2.3% |
| Miscellaneous | 2.5% | 2.8% | 6.6% |  | 1.7% |  |  |

LIQUID PHASE REACTION—FLASH PYROLYSIS

(Examples 20–29)

These reactions were done in a 250 ml 3-neck round bottom flask containing 50–70 ml of high boiling organic liquid. Purge gas ($N_2$, $N_2/SO_2$) at approximately 12 cc/minute served to transfer the pyrolysis products into a collection tube containing 10 ml of methanol cooled by a methanol/liquid nitrogen slurry.

The alpha-nitrotoluene was added at the rate of 0.2 ml/min. Variations and conditions used are recorded in Table III.

For Examples 27, 28 and 29 a condenser and uncooled receiver were used in place of the chilled trap. A heat gun was necessary in some cases to force the transfer of products that condensed or crystallized on the glassware between the flask and the collection tube. Samples were analyzed by glpc as previously described. Example 23 gave the best conversion to phenyl isocyanate (5.8%) at a volatiles recovery of 40%.

TABLE III

LIQUID PHASE REACTION-FLASH PYROLYSIS

| EXAMPLE | 20 | 21 | 22 | 23 | | 24 | | 25 | |
|---|---|---|---|---|---|---|---|---|---|
| Temp. Range | 200°–205° | 174°–178° | 172°–176° | 176°–180° | | 174°–178° | | 70° | |
| Gas | $N_2$ 12cc/min. Carried out in 250 ml 3 neck flask 2cc 0.2ml/min added to 50 ml mineral oil | $N_2$ 10cc/min. Carried out in 250 ml 3 neck flask 2cc 0.2ml/min added to 50 ml mineral oil | $N_2$ 10cc/min Same as Ex. 21 2cc .2ml added to 50 ml silicone oil | $N_2$ 10cc/min | | $N_2$ 10cc/min | | | |
| Pressure | | | | | | | | | |
| Amount of α-NT | 1.37 g | 1.37 g | 1.37 g | 1.37 g | | 1.60 g | | 1.38 g | |
| Product Color | Yellow | Colorless | Yellow | Colorless | | Colorless | | Yellow | |
| Reagent | 50 ml Nugol (mineral oil) | 50 ml Nugol (mineral oil) | 50 ml silicone oil | 50 ml silicone fluid 2g-toluene-sulfonic acid | | 50 ml mineral oil 2g p-toluene-sulfonic acid | | 10 ml toluene, 3 ml MeOH, 2 g, 3A + 0.2 g 5A MS | |
| % Recovery | 14.0% | 6.0% | 15.2% | 40.3% % | | 12.5% | | 94.1% | |
| | Comp. % | Comp. % | Comp. % | Conv. | Comp. % | % Conv. | Comp. % | % Conv. | Comp. % |
| α-Nitrotoluene | 4.8% | 1.9% | 7.5% | 80.4% | 48.6% | 93.2% | 54.4% | 20.3% | 85.2% |
| Phenyl Isocyanate | | | | 5.8% | 14.5% | 1.4% | 11.7% | | |
| Methyl Carbanilate | | Trace | 0.7% | 0.5% | 1.4% | | | 0.1% | 0.2% |
| Aniline | Trace | | 0.7% | 0.2% | 0.7% | 0.4% | 2.9% | | |
| Benzaldehyde | 3.2% | 2.1% | 2.0% | 0.5% | 1.4% | 0.1% | 0.5% | 1.8% | 1.9% |
| Benzyl Acetal | 0.5% | | | | | 0.4% | 2.9% | | |
| Methyl Benzoate | | | | 0.5% | 1.4% | 1.4% | 11.7% | 0.3% | 0.4% |
| Benzonitrile | 3.2% | 1.5% | 2.0% | | | 0.9% | 7.3% | 0.7% | 0.7% |
| Benzyl Alcohol | 0.2% | | 0.7% | 0.2% | 0.7% | | | | |
| Bibenzyl | | | | 0.2% | 0.7% | Trace | Trace | | |
| Stilbene | Trace | | Trace | Trace | Trace | | | | |
| Benzamide | 0.5% | | 0.7% | 0.8% | 2.1% | | | 2.5% | 2.7% |
| Oxadiazole | | | | | | 0.5% | 0.5% | | |
| α-Nitrostilbene | 1.1% | | | | | 0.7% | 0.7% | | |
| Miscellaneous | | | | 1.2% | 6.8% | | | 7.6% | 8.2% |

| | EXAMPLE | 26 | 27 | 28 | 29 |
|---|---|---|---|---|---|
| | Temp. Range | 170°–180° | 147°–149° | 185°–186° | 181°–184° |
| | Gas | $N_2$ very slow | $N_2$ 10cc/min. Bubbled | $N_2$ 10cc/min | $SO_2/N_2$ Mixture |
| | Pressure | 760 torr | 760 torr | 760 torr | 760 torr |
| | Amount of α-NT | 1.34 g | 1.33 g | 1.36 g | 1.33 g |
| | Product Color | None | Colorless | Yellow | Colorless |
| | Volume | 13.5 ml | | | |
| | Reagents | 2 g DNB 50 ml nitrobenzene | 70 ml DMF, 7 g P-TSA | 50 ml DMSO, 50 mg DNB, this method run twice, 2nd time air instead of $N_2$, DMSO 90% of product; the below were found in small amounts | Same as Ex. 28 3 runs with this: (a) + 2g Li Cl (b) + .5g $H_3PO_4$/air (c) + p-TSA/air |
| | % Recovery | 12.9% | | v. low | v. low |
| | | Comp. % | Comp. % | Comp. % | Comp. % |
| | α-Nitrotoluene | | 0.2% | X | X |
| | Phenylisocyanate | | | X | X |
| | Methylcarbanilate | | | X | X |
| | Aniline | | | | |
| | Benzaldehyde | | 83.6% | X | X |
| | Benzylacetal | | | | |
| | Methylbenzoate | | | | |
| | Benzonitrile | | 1.7% | X | X |
| | Benzylalcohol | | | | |
| | Bibenzyl | | | X | X |
| | Stilbene | | 8.6% | | |
| | Benzamide | 12.5% | 1.2% | X | X |
| | Oxadiazole | | 0.6% | X | X |

TABLE III-continued

| LIQUID PHASE REACTION-FLASH PYROLYSIS | | | |
|---|---|---|---|
| Nitrostilbene | 0.1% | X | X |
| Miscellaneous | 87.5% | | |

LIQUID PHASE REACTION—TWO PHASE
(Examples 30–33)

Two-phase reactions were performed in a 100 ml three neck round bottom flask with a nitrogen blanket flow of 10 ml/min. Each reaction was heated at reflux with vigorous stirring. Alpha-nitrotoluene (0.01 mol) was added when reaction temperature had been reached. Variations in the reagents, different strengths of sulfuric acid (5 M, 8 M and 9 M), and changes in the organic oil (carbon tetrachloride or chlorobenzene) are recorded in Table IV.

Very little reaction was observed in Examples 30 and 31. The major product in Examples 32 and 33 was benzoic acid, but significant amounts of benzyl chlorobenzene were produced as co-products as well. No aniline was detected by glpc in either the organic or aqueous extract.

TABLE IV

| | LIQUID PHASE REACTION - TWO PHASE AND SINGLE PHASE | | | | | |
|---|---|---|---|---|---|---|
| EXAMPLE | 30 | 31 | 32 | 33 | 34 | 35 |
| Method | Acid catalyzed Isomerization | Same as Ex. 30 | Same as Ex. 30 | Same as Ex. 30 | | |
| Temperature | 75° C. 2 hours | 112° C. 4 hours | 130° C. 4 hours | 130° C. 4 hours | 155° C. 1 hour | 150° C. 2 hours |
| Pressure | 760 torr | 760 torr | 760 torr | 760 torr | Max 80 psi | Max 50 psi |
| Gas | $N_2$ bubbled in at 10cc/min for duration | Same as Ex. 30 | Same as Ex. 30 | Same as Ex. 30 | $N_2$ bubbled 5 min. | $N_2$ bubbled 5 min. |
| Reagents | 1.37 g α-nitrotoluene 10ml $CCl_4$ + 50 ml 5M $H_2SO_4$ | Same as Ex. 30 Except 10 ml Chlorobenzene + 50 ml 5M $H_2SO_4$ | 1.37 g α-nitrotoluene 10 ml Chlorobenzene + 50 ml 8M $H_2SO_4$ 100 mg trioctylamine added at 1.5 hr. | 1.32 g α-nitrotoluene 10 ml Chlorobenzene + 50 ml 9M $H_2SO_4$ | 1.37 g α-NT 2 g anhyd. $CaCl_2$ 13 ml Dioxane 5 mg DNB | 1.37 g α-NT 1 g 3A + 1gm 5A Molec Sieves 13 ml Dioxane 50 mg DNB |
| % Recovery | | | | | 64.4% | 71.7% |
| | Comp. % | Comp. % | | | % Conv. Comp. % | % Conv. Comp. % |
| α-Nitrotoluene | 94.6% | 77.4% | 41.4% | 60.4% | 91.1% 13.8% | 87.5% 17.4% |
| Phenylisocyanate | 0.3% | | | | 1.5% 2.3% | 0.2% 0.3% |
| Methylcarbanilate | | | | | 0.2% 0.3% | 0.2% 0.3% |
| Benzaldehyde | 1.1% | 1.8% | 2.5% | 1.4% | 25.4% 39.5% | 26.8% 37.4% |
| Benzylacetal | | | | | 2.1% 3.2% | |
| Methylbenzoate | | | 3.0% | | | |
| Aniline | | | | | | |
| Benzonitrile | 0.8% | 1.6% | 0.5% | 1.4% | 16.5% 15.7% | 16.0% 22.4% |
| Benzaldoxime | | | 8.2% | 8.0% | | |
| Bibenzyl | | | | | 0.5% 0.9% | 0.8% 1.2% |
| Stilbene | | | | | Trace Trace | 0.2% 0.3% |
| Benzamide | 0.3% | 1.0% | | 0.4% | 3.6% 5.6% | 5.9% 8.3% |
| Oxadiazole | 0.7% | 1.2% | 0.6% | 1.0% | 1.9% 2.9% | 4.2% 5.8% |
| Nitrostilbene | 0.3% | 0.5% | | 1.0% | Trace Trace | 1.5% 2.1% |
| Benzoic Acid | | 14.6% | 39.1% | 21.4% | 0.9% 1.4% | 0.2% 0.3% |
| Furoxan | | | | Trace | Trace Trace | 0.4% 0.6% |
| Miscellaneous | | | 9.8% | 8.0% | 2.1% 3.2% | 1.0% 1.5% |

| EXAMPLE | 36 | 37 |
|---|---|---|
| Method | Acid catalyzed Isomerization | Same as Ex. 36 |
| Temperature | 80° C. 4 hours | 80° C. 7 hours |
| Pressure | 760 torr | 760 torr |
| Gas | | |
| Reagents | 4.11 g α-nitro toluene 10 ml EtOH 5 ml 30% HCl | 2.73 g α-nitro toluene 1 ml EtOH 5 ml 30% HCl |
| Mass Balance | 92% | 46.8% |
| | % Conv. Comp. % | % Conv. Comp. % |
| α-Nitrotoluene | 20.0% 59.5% | 68.0% 70.0% |
| Phenylisocyanate | 15.4% 3.2% | 2.9% 2.7% |
| Methylcarbanilate | 2.4% 0.6% | 1.0% 1.4% |
| Benzaldehyde | 1.7% | |
| Benzylacetal | | |
| Methylbenzoate | | |
| Aniline | 1.4% 0.3% | trace |
| Benzonitrile | 13.3% 10.4% | 4.0% 6.0% |
| Benzylalcohol | | |
| Bibenzyl | | |
| Stilbene | | |
| Benzamide | 13.7% 3.3% | 5.7% 7.2% |

TABLE IV-continued

| LIQUID PHASE REACTION - TWO PHASE AND SINGLE PHASE | | | | | |
|---|---|---|---|---|---|
| | Oxadiazole | 5.2% | 1.2% | 1.6% | 2.2% |
| | Nitrostilbene | 5.4% | 1.5% | 0.6% | 0.7% |
| | Benzoic Acid | 3.3% | 2.0% | 6.0% | 6.0% |
| | Furoxan | | | | |
| | Miscellaneous | | | | |

LIQUID PHASE REACTION—SINGLE PHASE (Examples 34–37)

Examples 34 and 35 were performed in the pressure reactor at 150° C. Nitrogen was bubbled through the reactor in each case for five minutes prior to sealing and heating. The reagents are listed in Table IV. Samples were taken after the reactor was opened and analyzed by glpc. Benzaldehyde and benzonitrile were the major products with Example 34 yielding 1.5% conversion to phenyl isocyanate.

Examples 36 and 37 were conducted at 80° C. under reflux for four hours and seven hours in a 50 ml three neck round bottom flask outfitted with a reflux condenser. Samples were removed at timed intervals and analyzed by glpc. The major products formed were phenylisocyanate (15.4%), benzonitrile (13.3%) and benzamide (13.7%) in Example 36 and phenylisocyanate (2.9%), benzonitrile (4.0%), benzamide (5.7%) and benzoic acid (6.0%) in Example 37. After the third hour of heating, Example 37 formed two layers; a brown organic, and a bluish-green aqueous layer. The four and seven hour samples were taken from the organic layer.

LIQUID PHASE REACTION-SOLID CATALYST REACTION (Examples 40–66)

Example 45 was carried out at reflux (70° C.) for 16 hours in a 50 ml three neck round bottom flask with attached reflux condenser. The total volatile recovery was good (94%), but there was little conversion of nitrotoluene.

The remaining examples 40–44 and 46–66 were carried out in the Parr pressure reactor at various temperatures and pressures; various gases were used to either purge the reactor by bubbling through the liquid phase or to purge and pressurize the reactor. Samples were drawn off at timed intervals through the sampling system and analyzed by glpc. In some cases low recoveries were the result of reactor leaks.

TABLE V

LIQUID PHASE REACTION - SOLID CATALYST

| EXAMPLE | 40 | 41 | 42 | 43 | 44 | 45 | 46 |
|---|---|---|---|---|---|---|---|
| Temp. Range | Max. 138° | Max. 138° | Max 136° | 130°-140° | Max. 150° C. | 70° C. | 140-150° C. 1 hour |
| Gas | 5 min. Purge w/N₂ | Same as Ex. 40 | Sample bubbled w/SO₂ | Taken at shutdown | | | SO₂ bubbled for 15 min. pressurized |
| Pressure | 120 psi | 125 psi | Max. 100 psi | 120 psi | Max 170 psi | Max 170 psi | Max. 200 psi |
| Amount of α-NT | 1.38 g | 1.37 g | 1.37 g | 1.37 g | 1.37 g | 1.38 g | 1.47 g |
| Product Color | Dark Green | Yellow | Dark Yellow | Dark Yellow | Yellow | Yellow | Brown (reddish) |
| Reagents | 2 g 3A MS 0.2 g 5A MS 10 ml toluene, 3 ml MeOH | Same as Ex. 40 | Same as Ex. 40 | 2 g 3A MS 0.2 g 5A MS 10 ml toluene, 3 ml MeOH | No molecular sieves used, 10 ml toluene, 3 ml MeOH | 10 ml toluene, 3 ml methanol, 100 mg DNB, 2 g 3A MS, 0.2 g 5A MS | Same as Ex. 45 |
| % Recovery | 30.2% | 17.4% | 73.3% | 27.4% | 27.4% | 94.1% | 49.4% |
| | % Conv. Comp. % | % Conv. Comp. % | % Conv. Comp. % | % Conv. Comp. % | % Conv. Comp. % | % Conv. Comp. % | % Conv. Comp. % |
| α-Nitrotoluene | 23.0% | 8.5% | 17.1% | 9.2% | trace | 20.3% | 80.0% 9.9% |
| Phenylisocyanate | 0.6% | 0.6% | 2.3% | 1.2% | 6.4% | 0.1% | |
| Methylcarbanilate | 8.2% | 13.1% | 13.7% | 9.8% | 2.8% | | 8.5% 4.2% |
| Aniline | 1.7% | 3.2% | 1.9% | 2.4% | 14.1% | 1.8% | |
| Benzaldehyde | 7.6% | 10.4% | 9.5% | 11.0% | 9.8% | | 12.6% 6.2% |
| Benzylacetal | 6.5% | 6.5% | 3.4% | 10.4% | 7.8% | 0.3% | 27.2% 13.4% |
| Methylbenzoate | 7.1% | 8.4% | 5.7% | 6.1% | 22.7% | 0.7% | 3.3% 1.6% |
| Benzonitrile | 8.2% | 11.7% | 12.6% | 19.6% | 8.5% | | 19.4% 9.6% |
| Benzylalcohol | | | 2.6% | 4.9% | 2.1% | | 0.7% 0.4% |
| Bibenzyl | 1.1% | 2.0% | 1.1% | | 0.2% | trace | 0.2% 0.1% |
| Stilbene | | 4.5% | 4.2% | 3.1% | 5.6% | 2.5% 2.7% | 1.5% 0.7% |
| Benzamide | 13.6% | 11.7% | 8.7% | 3.7% | 3.5% | 0.5% 0.5% | 1.3% 0.6% |
| Oxadiazole | 7.1% | 8.5% | 3.4% | 3.1% | 2.1% | 0.7% 0.7% | 0.3% 0.2% |
| Nitrostilbene | 7.1% | 3.9% | 3.0% | trace | 14.1% | 7.6% 8.2% | 3.8% 0.9% |
| Miscellaneous | 2.9% | 3.9% | 10.3% | 13.4% | | | |

| EXAMPLE | 47 | 48 | 49 | 50 | 51 | 52 | 53 |
|---|---|---|---|---|---|---|---|
| Temp. Range | 100° ± 50° C. 2 hours | 125° C. | 150° C. | 150° C. | 125° C. | 150° C. | 95° C. 5 hours |
| Gas | SO₂ bubbled for 15 min. bomb pressurized to 35 psi | SO₂ bubbled for 15 min; bomb pressurized to 30 psi | Same as Ex. 48 | SO₂ bubbled not pressurized | Same as Ex. 50 | SO₂ bubbled through 15 min | N₂ blanket less than 10cc/min |
| Pressure | 115 psi | 125 psi | 160 psi | 240 psi | 180 psi | 150 psi | |
| Amount of α-NT | 1.44 g | 1.40 g | 1.40 g | 1.47 g | 1.46 g | 1.47 g | 1.40 g |
| Product Color | Dark Yellow | Yellow | Dark Brown | Dark Brown | Yellow | Amber | Yellow |
| Reagents | Same as Ex. 46 | Same as Ex. 46 | 2 g of CaSO₄ in place of MS, all else same as Ex. 46 | Same as Ex. 49 | Same as Ex. 49 | 2 g hydrogen mordenite, 10 ml toluene, 100 mg DNB | 2 g H. mordenite 10 ml tol., 100 mg DNB, 3 ml-N-Propanol |
| % Recovery | 72.1% | 65.3% | 86.8% | 94.6% | 81.1% | 71.0% | 92.4% |
| | % Conv. Comp. % | % Conv. Comp. % | % Conv. Comp. % | % Conv. Comp. % | % Conv. Comp. % | % Conv. Comp. % | % Conv. Comp. % |
| α-Nitrotoluene | 39.7% 83.6% | 56.5% 66.7% | 97.3% 3.0% | 2.6% 2.7% | 40.8% 73.0% | 42.7% 80.7% | 10.5% 88.0% |

TABLE V-continued

LIQUID PHASE REACTION - SOLID CATALYST

| | 54 | | 55 | | 56 | | 57 | | 58 | | 59 | | 60 | |
|---|---|---|---|---|---|---|---|---|---|---|---|---|---|---|
| Phenylisocyanate | 0.2% | | 0.1% | | 6.0% | | 0.4% | | 0.3% | | 2.0% | | 1.0% | |
| Methylcarbanilate | | | 0.1% | | trace | | 21.2% | | | | 0.5% | | | |
| Aniline | | 0.4% | 0.6% | | 19.4% | | 13.6% | 22.4% | 2.2% | | 1.8% | 2.8% | 1.2% | 1.0% |
| Benzaldehyde | 1.0% | 1.4% | 4.4% | 6.7% | 26.0 | 22.3% | 28.3% | 14.4% | 9.7% | 2.7% | 0.1% | 0.6% | 0.3% | 1.2% |
| Benzylacetal | 3.3% | 4.6% | 7.7% | 11.8% | 5.0% | 29.9% | 9.2% | 29.9% | 1.6% | 12.0% | 2.1% | 2.5% | 0.1% | 0.3% |
| Methylbenzoate | 0.2% | 0.4% | 0.7% | 1.2% | 17.6% | 5.7% | 10.1% | 9.7% | 2.5% | 2.0% | 1.0% | 3.0% | trace | trace |
| Benzonitrile | 1.5% | 2.2% | 2.2% | 3.3% | 0.4% | 20.2% | 0.2% | 10.7% | trace | 3.1% | trace | 1.3% | 0.7% | 0.7% |
| Benzylalcohol | 0.1% | 0.2% | 0.1% | 0.1% | 0.6% | 0.4% | 0.4% | 0.2% | | trace | 0.2% | trace | 0.2% | 0.2% |
| Bibenzyl | | | trace | trace | 2.6% | 0.7% | 0.7% | 0.5% | trace | trace | 0.4% | 0.6% | 0.7% | 0.7% |
| Stilbene | 0.7% | 1.0% | 0.9% | 1.3% | 1.8% | 3.0% | 0.7% | 0.7% | 0.7% | 0.9% | 0.2% | 0.3% | 0.7% | 0.7% |
| Benzamide | 0.4% | 0.6% | 0.9% | 1.3% | | 2.0% | | 0.7% | 0.2% | 0.2% | 0.4% | 0.5% | 0.3% | 0.3% |
| Oxadiazole | 0.2% | 0.5% | 0.2% | 0.5% | | | | | 0.1% | 0.2% | 0.2% | 0.3% | 0.5% | 0.5% |
| Nitrostilbene | 3.6% | 5.0% | 2.1% | 3.2% | 2.8% | 3.2% | 4.9% | 5.2% | 3.3% | 4.0% | 4.3% | 6.0% | 6.3% | 6.2% |
| Dinitrobenzene | 3.6% | 5.0% | 1.3% | 2.0% | | | | | | | | | | |
| Miscellaneous | | | | | | | | | | | | | | |

| EXAMPLE | 54 | 55 | 56 | 57 | 58 | 59 | 60 |
|---|---|---|---|---|---|---|---|
| Temp. Range | 95° C. 7 hours | 150° C. 3 hours | 148–152° C. 3 hours | 150–153° C. 3 hours | 135–177° C. | 150° C. | 146–154° C. 2½ hours |
| Gas | N₂ 10 cc/min | SO₂ bubbled for 15 min. | SO₂ bubbled; 15 min. | Same as Ex. 56 | Zero air, 15 min. bubbling | O₂ bubbled in for 15 min. | N₂ bubbled 15 min. |
| Pressure | None | 230 | Max 220 psi | Max 220 psi | Max 80 psi | Max 80 psi | Max 180 psi |
| Amount of α-NT | 1.39 g | 1.40 g | 1.39 g | 1.37 g | 1.38 g | 1.38 g | 1.38 g |
| Product Color | Amber | Brown | Dark Olive Green | Brown | Brown | Brown | Brown |
| Reagents | Same as Ex. 53 | Same as Ex. 52 | 2 g Nalcat low alumina catalyst 100 ml toluene 3 ml MeOH 100 mg DNB | 2 g high alumina catalyst 100 ml toluene 3 ml MeOH 100 mg DNB | Same as Ex. 56 Except 50 mg DNB | Same as Ex. 56 50 mg DNB | 2 g Nalcat low alumina catalyst 100 ml toluene 3 ml MeOH 50 mg DNB |
| % Recovery | 98.5% | 26.9% | 80.7% | 70.0% | 50.0% | 35.6% | 62.1% |

| | % Conv. | Comp. % | % Conv. | Comp. % | % Conv. | Comp. % | % Conv. | Comp. % | % Conv. | Comp. % | % Conv. | Comp. % | % Conv. | Comp. % |
|---|---|---|---|---|---|---|---|---|---|---|---|---|---|---|
| α-Nitrotoluene | 11.5% | 8.7% | 97.7% | | 84.9% | 18.8% | 98.6% | 2.0% | 98.3% | 3.4% | 98.8% | 3.4% | 96.5% | 5.6% |
| Phenylisocyanate | | | | | trace | trace | | | | | 0.2% | 0.5% | | |
| Methylcarbanilate | 1.0% | 0.6% | 3.1% | 11.8% | 17.7% | 21.0% | 4.2% | 6.1% | 0.6% | 1.2% | 0.3% | 0.8% | 2.5% | 4.0% |
| Aniline | | | | | | | | | | | | | | |
| Benzaldehyde | 0.6% | 0.6% | 1.2% | 4.5% | 8.9% | 11.1% | 11.4% | 16.3% | 14.3% | 28.7% | 9.4% | 26.5% | 15.5% | 25.0% |
| Benzylacetal | 0.4% | 0.4% | 6.2% | 23.0% | 12.6% | 15.6% | 16.7% | 23.9% | 0.5% | 1.0% | 0.2% | 0.5% | 0.4% | 0.6% |
| Methylbenzoate | | | 4.4% | 16.3% | 6.9% | 8.5% | 5.9% | 8.4% | 5.0% | 10.1% | 2.0% | 5.8% | 7.1% | 11.4 |
| Benzonitrile | 0.4% | 0.4% | 2.8% | 10.4% | 11.5% | 14.2% | 15.7% | 22.4% | 10.6% | 21.2% | 7.3% | 20.6% | 9.3% | 15.1% |
| Benzylalcohol | 0.4% | 0.4% | | | trace | trace | 0.2% | 0.3% | 0.3% | 0.7% | 0.5% | 1.4% | 0.3% | 0.4% |
| Bibenzyl | | | | | 0.2% | 0.2% | 0.2% | 0.3% | 0.3% | 0.7% | 0.7% | 2.0% | 0.4% | 0.7% |
| Stilbene | trace | trace | 0.4% | 1.4% | trace | trace | 0.8% | 1.1% | 0.8% | 1.7% | 0.8% | 2.3% | 1.2% | 2.0% |
| Benzamide | trace | trace | 1.5% | 5.5% | 2.0% | 2.5% | 2.4% | 3.5% | 4.2% | 8.4% | 3.4% | 9.9% | 5.9% | 9.4% |
| Oxadiazole | 0.4% | 0.4% | 0.4% | 1.4% | 0.5% | 0.5% | 2.0% | 2.9% | 2.9% | 5.9% | 2.6% | 7.5% | 5.3% | 8.9% |
| Nitrostilbene | trace | trace | | | 0.2% | 0.2% | 0.7% | 0.8% | 0.6% | 1.2% | 0.7% | 3.4% | 1.1% | 1.8% |
| Dinitrobenzene | 6.7% | 6.7% | 1.5% | 5.5% | 3.4% | 4.2% | 3.2% | 4.6% | 5.0% | 9.9% | 2.1% | 6.1% | 2.9% | 4.7% |
| Miscellaneous | | | | | 1.4% | 1.9% | 2.4% | 3.5% | | | 2.1% | 3.3% | 2.1% | 3.3% |

| EXAMPLE | 61 | 62 | 63 | 64 | 65 | 66 |
|---|---|---|---|---|---|---|
| Temp. Range | 145° C. 3 hours | 150–180° C. 3 hours | 150° C. 1 hour | 150° C. ½ hour | 150° C. ± 3° C. 1¼ hr. | 150° C. 1 hour |
| Gas | SO₂ bubbled | SO₂ bubbled | Pressurized to | Pressurized to | SO₂ bubbled | SO₂ bubbled 5 min. |

TABLE V-continued

LIQUID PHASE REACTION - SOLID CATALYST

| | | | | 10 psi with SO₂ | | | | | | | |
|---|---|---|---|---|---|---|---|---|---|---|---|
| Pressure | 15 min. Max. 190 psi | | 15 min. Max. 200 psi | | Max. 200 psi | | 15 min. Max. 210 psi | | Max. 240 psi | | Max. 230 psi | |
| Amount of α-NT | 1.37 g | | 1.38 g | | 1.38 g | | 1.38 g | | 1.38 g | | 1.37 g | |
| Product Color | Brown | | Brown | | Olive | | Brown | | Brown | | Brown | |
| Reagents | 2 g silica gel 50 mg DNB 10 ml toluene 3 ml MeOH | | 2 acidic alumina 50 mg DNB 10 ml toluene 3 ml MeOH | | Same as Ex. 62 | | 2 g acidic alumina 50 mg DNT 10 ml toluene 3 ml MeOH | | 50 mg DNT 2 g CaCl₂ 10 ml toluene 3 ml MeOH | | Same as Ex. 65 | |
| % Recovery | 55.2% | | 75.8% | | 87.8% | | 73.9% | | 65.9% | | 75.5% | |
| | % Conv. | % Comp. | % Conv. | Comp. % | % Conv. | Comp. % | % Conv. | Comp. % | % Conv. | Comp. % | % Conv. | Comp. % |
| α-Nitrotoluene | 96.4% | 6.5% | 98.0% | 2.6% | 65.8% | 39.8% | 96.5% | 4.7% | 96.6% | 5.2% | 94.6% | 7.1% |
| Phenylisocyanate | | | | | | | | | 1.7% | 2.6% | 3.0% | 4.0% |
| Methylcarbanilate | 9.4% | 16.9% | 9.4% | 12.4% | 13.0% | 14.0% | 12.3% | 16.7% | 4.0% | 6.0% | 5.9% | 7.8% |
| Aniline | 0.2% | 0.3% | | | | | | | | | | |
| Benzaldehyde | 9.2% | 16.6% | 11.0% | 14.5% | 9.6% | 11.0% | 10.3% | 14.0% | 10.0% | 15.2% | 13.4% | 17.8% |
| Benzylacetal | 3.8% | 6.8% | 21.0% | 27.7% | 8.8% | 10.0% | 14.5% | 19.6% | 21.6% | 32.8% | 20.2% | 26.8% |
| Methylbenzoate | 10.4% | 18.8% | 7.6% | 10.0% | 4.4% | 5.0% | 6.3% | 8.6% | 5.9% | 8.9% | 5.0% | 6.5% |
| Benzonitrile | 8.3% | 15.0% | 14.6% | 19.2% | 8.4% | 9.5% | 12.5% | 16.9% | 16.9% | 25.6% | 15.8% | 20.9% |
| Benzylalcohol | 0.9% | 1.6% | 0.4% | 0.5% | 0.2% | 0.2% | 0.4% | 0.6% | | | 0.5% | 0.6% |
| Bibenzyl | 0.2% | 0.3% | 0.2% | 0.2% | 0.2% | 0.3% | 0.2% | 0.3% | | | 1.1% | 1.5% |
| Stilbene | 0.9% | 1.6% | 0.8% | 1.0% | | | 0.8% | 1.2% | 0.5% | 0.8% | | |
| Benzamide | 2.9% | 5.2% | 2.4% | 3.1% | 2.1% | 2.3% | 2.2% | 2.9% | trace | trace | trace | trace |
| Oxadiazole | 1.2% | 2.2% | 1.0% | 1.3% | 0.8% | 0.9% | 1.5% | 2.0% | 0.7% | 1.1% | 1.4% | 1.8% |
| Nitrostilbene | | | 0.6% | 0.8% | 0.4% | 0.4% | 0.6% | 0.6% | | | trace | trace |
| Dinitrobenzene | 2.0% | 3.5% | 1.6% | 2.1% | 2.1% | 2.4% | 1.5% | 2.0% | | | 0.7% | 0.9% |
| Miscellaneous | | | 1.6% | 2.1% | 1.9% | 2.1% | 2.2% | 3.0% | | | 1.1% | 1.5% |

As the above data in the tables reveal, we have discovered a method for performing the dehydration-isomerization of nitromethyl aromatic compounds to aromatic isocyanates or their interconvertible alcohol adducts, the carbamates, in essentially one step. The isomerization-dehydration reaction is performed without consumption of expensive reagents such as carbon monoxide, chlorine or hydrogen. This new route to organic isocyanates affords the opportunity to provide chlorine-free isocyanate products for coating and other markets where metal corrosion is a problem. In addition, the inventive process offers an inherent benefit of being energy efficient; there is no overreduction and then reoxidation as in the conventional routes. Since the novel process basically comprises one step, it may provide up to a two processing step advantage over either the phosgene or carbonylation routes to isocyanates. Furthermore, the production of large quantities of hydrogen chloride or carbon dioxide by-products is also avoided and high pressures or specially corrosion resistant materials of plant construction are not required.

Additionally, the dehydration-isomerization reaction of nitromethyl aromatic compounds using Lewis acids or Bronsted acids offers a means for producing phenylene diisocyanate and phenyl isocyanate from xylene and toluene, respectively. Both the prior art phosgenation and carbonylation methods used expensive benzene to produce these isocyanates.

Toluene diisocyanate and methylenediphenyl diisocyanate in a mixture with its higher oligomers, polymethylenepolyphenylene isocyanate, comprise the majority of isocyanates sold in the United States and throughout the world. Again, the method of this invention allows the use of toluene rather than benzene in the production route to methylenediphenyl diisocyanate and polymethylenepolyphenylene isocyanate. This new route would comprise the alpha-nitration of toluene to produce alpha-nitrotoluene which is then subjected to the dehydration-isomerization reaction of this invention to afford phenyl isocyanate. Reaction of the isocyanate with an alcohol would yield the corresponding carbanilate product which could then be dimerized or polymerized through the use of formaldehyde and acidic catalysis. See U.S. Pat. Nos. 2,946,768 and 4,202,986 which are incorporated by reference.

By an analogous reaction route phenylene diisocyanate could be produced from a xylene. The xylene material is nitrated to afford a di(nitromethyl)-benzene compound which is then subjected to the dehydration-isomerization reaction of this invention to yield the phenylene diisocyanate. Accordingly, it is now possible to produce phenylene diisocyanate under mild, less expensive conditions than are required for the conventional route proceeding via the difficult dinitration of benzene to dinitrobenzene.

Furthermore, the phenylene diisocyanate or the phenyl isocyanate could then be subjected to hydrolysis to yield an aromatic diamine or aniline. Thus, the process of this invention could provide a new overall route to the production of aromatic diamines from xylene and aniline from toluene.

STATEMENT OF INDUSTRIAL APPLICATION

The process of this invention provides an attractive method for producing aromatic isocyanates which find their primary use as intermediates in the manufacture of polyurethanes. The isocyanate intermediates can now be produced from the less expensive and much less toxic compound toluene.

What is claimed is:

1. A process for the preparation of an aromatic isocyanate which comprises heating a compound of the general formula I:

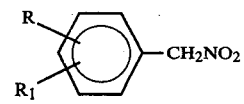

wherein R and $R_1$ represent hydrogen, halogen, nitro, a $C_1$-$C_5$ alkyl radical, a $C_1$-$C_4$ alkoxy radical, isocyanato, an alkoxycarbonylamino radical of the formula —NH—COOR$_2$ wherein $R_2$ represents a $C_1$-$C_5$ alkyl radical, or a nitromethyl radical, with R and $R_1$ being the same or different, in the presence of an effective amount of a Lewis acid or Bronsted acid substance to yield an aromatic isocyanate of the general formula II:

wherein R and $R_1$ are the same as above and provided that if R or $R_1$ were a nitromethyl radical in the general formula I, such R or $R_1$ now represents an isocyanato group.

2. The process of claim 1 wherein the aromatic isocyanate is recovered in an alkyl alcohol-containing medium as an alkyl carbamate of the general formula III:

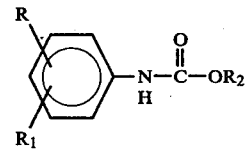

wherein R, $R_1$, and $R_2$ are the same as before; provide that if R or $R_1$ represented an isocyanato group in general formula II, such R or $R_1$ now represents an alkyl carbamate group of the formula —NH—COOR$_2$.

3. The process of claims 1 or 2 wherein R and $R_1$ represent hydrogen, halogen, a $C_1$-$C_3$ alkyl radical or a nitromethyl radical.

4. The method of claims 1 or 2 wherein R is a nitromethyl radical and $R_1$ is hydrogen and the recovered product is a phenylenediisocyanate or the carbamate ester of a phenylenediisocyanate.

5. The method of claims 1 or 2 wherein R and $R_1$ are hydrogen and the recovered product is phenylisocyanate or an alkyl carbanilate.

6. The method of claim 2 wherein $R_2$ is methyl.

7. The process of claim 1 wherein the nitromethyl aromatic compound is xylene, and the aromatic isocyanate is phenylene diisocyanate.

8. The process of claim 1 in which the nitromethyl aromatic compound is alpha-nitrotoluene, and the aromatic isocyanate is phenyl isocyanate.

9. The process of claim 2 wherein the nitromethyl aromatic compound is alpha-nitrotoluene and the alkyl carbamate is methyl carbanilate.

10. The process of claims 1, 2, 7, 8 or 9 wherein the Lewis acid or Bronsted acid substance is calcium sulfate.

11. The process of claim 10 which includes sulfur dioxide.

12. The process of claims 1, 2, 7, 8 or 9 wherein the Lewis acid or Bronsted acid substance is p-toluenesulfonic acid.

13. The process of claims 1, 2, 7, 8 or 9 wherein the Lewis acid or Bronsted acid substance is a zeolite molecular sieve.

14. The process of claim 13 wherein the zeolite sieve is a 3 A molecular sieve.

15. The process of claims 1, 2, 7, 8 or 9 wherein the Lewis acid or Bronsted acid substance is hydrochloric acid.

16. A process for the preparation of an aromatic isocyanate which comprises heating at a temperature from about 50° to 500° C. a compound of the general formula I:

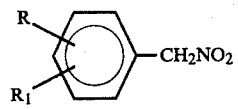

wherein R and $R_1$ simultaneously or independently represent hydrogen or nitromethyl, in the presence of an effective amount of a Lewis acid or Bronsted acid substance to yield an aromatic isocyanate of the general formula II:

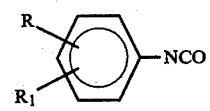

wherein R and $R_1$ now simultaneously or independently represent hydrogen or isocyanato.

* * * * *